Aug. 13, 1974 A. BARBERET ET AL Plant Pat. 3,592
CARNATION PLANT
Filed March 30, 1973
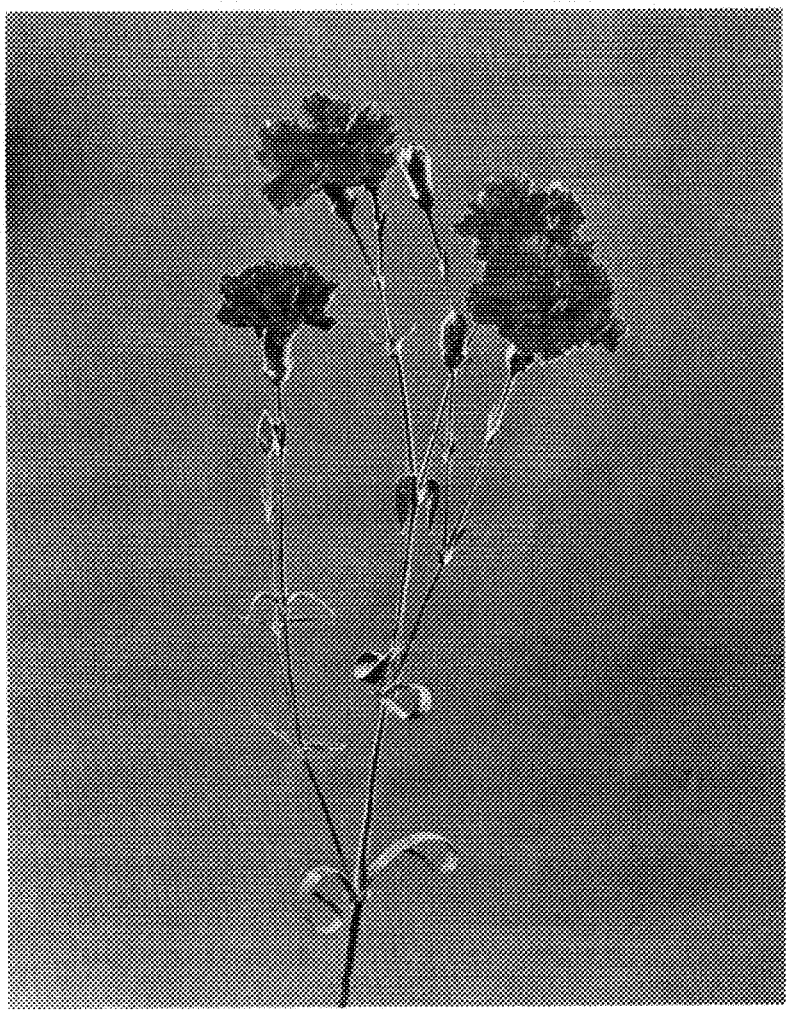

United States Patent Office

Plant Pat. 3,592
Patented Aug. 13, 1974

3,592

CARNATION PLANT

Alexandre Barberet and Henri Blanc, La Londe, France, assignors to Laboratoire de Physiologie Vegetale de la Londe Barberet & Blanc, La Londe, France Filed Mar. 30, 1973, Ser. No. 346,715
Int. Cl. A01h 5/00
U.S. Cl. Plt.—72 1 Claim

ABSTRACT OF THE DISCLOSURE

A new variety of carnation plant of the miniature type suitable for greenhouse production of cut flowers and most nearly resembling the miniature variety "Sam's Pride," this new variety being distinguished by the darker and bluish coloring of its flowers, the smaller size of its flowers which have fewer but more frilly petals, and its shorter and more rigid flower stems.

BACKGROUND OF THE NEW PLANT

This new variety of carnation plant was selected by us in 1969 from a group of seedlings resulting from a crossing of two unnamed varieties from the collection of carnation plants maintained in our laboratories at La Londe, France, for breeding and developmental purposes. One of the objects of the breeding program is to develop new and improved varieties of carnations for the commercial market and in the present instance, to provide a variety with better yield and well branched inflorescence in wintertime. This new variety was selected because it appeared to have the characteristics being sought, as well as to be a material improvement over the variety "Sam's Pride" (unpatented), and asexual propagation of the new variety under our direction and by means of cuttings at La Londe, France, has shown its novel and distinctive characteristics to remain true from generation to generation and to be firmly fixed.

DESCRIPTION OF THE DRAWING

Our new variety of carnation plant is illustrated by the accompanying full color drawing which shows inflorescence of the new plant, including buds, partially opened flowers and full opened blossoms, in color as true as it is reasonably possible to obtain by conventional photographic procedures.

DESCRIPTION OF THE NEW PLANT

The following is a detailed description of our new variety of carnation plant according to observations made on Jan. 12, 1973, of greenhouse plants of the new variety set out in April 1972 at La Londe, France, with color designations according to the R.H.S. Colour Chart of the Royal Horticultural Society at London, England.

*The plant*

Origin: Seedling.

Parentage:

*Seed Parent.*—7V2, unnamed, unpatented.

*Pollen Parent.*—Ger-Mini, unnamed, unpatented. There are plants in my collection at La Londe, France, that are identified by the above stated numbers in my permanent records.

Classification:

*Botanic.*—Hybrid Dianthus caryophyllus L.

*Commercial.*—Spray carnation for cut flowers.

Form: Leafy bush of the Sim type.

Height: Flowers appear up to about 92 cm. above the soil.

Growth: Vigorous and erect.

Branching: Normal—sturdy and upright with 5 to 8 primary stems per plant, each about 82 cm. long and well branched with about 4 secondary floral stems, each of which has at least 2 flowers.

Foliage: Quantity—Abundant, quite dense at the base and in a 10-months old plant, rising in tiers as far as 40 cm. from the ground.

*Size of Leaf.*— Up to 15 cm. long and up to 0.9 cm. wide, the longest leaves most often appearing between the 9th and 13th nodes or joints of the stem and the widest leaf most often at the 5th node.

*Shape of Leaf.*—Lanceolate and often with a dried extremity about 1 cm. long. The leaves extend upwardly from the stem then curve or coil downwardly. Near the stem the leaves are amplexicaul and decurrent, becoming more-or-less flat length wise and terminating with scabious tip end.

*Texture:* Smooth.

*Color:* Leaves—Greyed Green 189 B. Nodes—Yellow Green 145 C. Stems—Greyed Green 189B.

*The bud*

Calyx:

*Form.*—Ovoid and perfectly symmetrical; sharp pointed at the beginning of its development, becoming long—ovoid and then funnel shaped as sepals open.

*Size.*—Medium. 30 mm. long before opening.

*Number per Inflorescense.*—6 to 8 buds and flowers.

*Opening.*—Bud opens rather rapidly.

*Sepals.*—Upstanding. Ovoid in shape and 5 in number. Color: Inside.—Pale Green; outside—Light green.

*Aspects.*—Smooth and calyx does not split.

Color of Flower Bud: Red Purple when sepals first divide and begin to unfurl.

*The flower*

Blooming Habit: Continuous and profusely. The flowers open more-or-less sequentially without precise order or regularity.

Size of Bloom: Small. Average diameter—5.1 cm. average depth—2.3 cm.

Borne: Singly in spray arrangement on relatively short, stiff stems.

Shape: High centered when bloom first opens and shape does not change.

Petalage: 32 to 45 petals, averaging about 37 in number, in more-or-less imbricated arrangement.

*Form of Petals.*—Fan shaped with margins more-or-less puckered or ruffled and having irregular indentations which give the flower a frilly aspect.

*Color.*—The general color aspect of the flower is Deep Pink or Rose Cerise, becoming less intense and more bluish toward the margins of the petals as the bloom matures.

Coloring of the blossom petals:

| | Upper side | Reverse side |
|---|---|---|
| Young flowers | Red Purple 57A | Red Purple 57C. |
| Full bloom | Red Purple 57B | Red Purple 57C. |

Appearance: Satiny Texture: Soft

Petaloids: About 8 in number, half the size of petals. *Color.*—Deep Pink.

Peduncle: Erect and rigid. Up to 17 cm. long. *Color.*—Greyed Green.

Fragrance: Faintly perceptible.

Effect of Weather: None

Persistence: Petals hang on and dry.

Disease Resistance: Good, for all common diseases of carnations as observed at La Londe, France.

Lasting Quality: On plant—20 days. As cut flower—15 days.

*Reproductive organs*

Stamens: Anthers—Plus or minus 10 in summertime, 2 to 3 mm. long. Filaments—2.5 cm. long. Color—White. Pollen—Yellowish in color.
Pistils: 2 in number. Styles: 3.5 cm. when ripe.
Stigmas: Color—White and Reddish.
Ovaries: Cone shaped.

*Fruit*

The fruit is fertile in summertime and is pear shaped. The color at maturity is Green and Ocherous.

This new variety of carnation plant is particularly distinguished from Sam's Pride (unpatented), the plant it most nearly resembles, in that it is more precocious than Sam's Pride, has a better spray growth and arrangement, is more compact and erect, and the flowers have a more brilliant color and are smaller, all of which gives the new variety important advantages for commercial scale propagation and for buyer acceptance by those who favor carnation flowers.

Other advantages of this new carnation variety reside in very good branching with rather short and rigid peduncles, its petite and lively colored flowers, the particular formation of the petals of the fully opened flower which gives the blossom a very attractive frilly appearance, the very excellent productivity of the new variety, and its good lasting quality as a cut flower.

We claim:

1. A new and distinct variety of carnation plant, substantially as herein shown and described, characterized by the distinctive coloring of its flowers which are carried on short stiff stems, and its prolific production of inflorescence which provides many successively opening flowers having excellent lasting qualities as cut flowers.

No references cited.

ROBERT E. BAGWILL, Primary Examiner